(12) United States Patent  (10) Patent No.: US 8,079,574 B2
Lin  (45) Date of Patent: Dec. 20, 2011

(54) MEMBRANE BASED CONTACTOR MODULE FOR MASS AND HEAT TRANSFER

(75) Inventor: Zhenwu Lin, Hangzhou (CN)

(73) Assignee: ZenPure Corp., Bellevue, WA (US)

( * ) Notice: Subject to any disclaimer, the term of this patent is extended or adjusted under 35 U.S.C. 154(b) by 1241 days.

(21) Appl. No.: 11/803,890

(22) Filed: May 16, 2007

(65) Prior Publication Data

US 2011/0285038 A1    Nov. 24, 2011

(51) Int. Cl.
B01F 3/04 (2006.01)
(52) U.S. Cl. .................................................. 261/104
(58) Field of Classification Search .................. 261/104, 261/107
See application file for complete search history.

(56) References Cited

U.S. PATENT DOCUMENTS

| | | | | |
|---|---|---|---|---|
| 4,060,576 A | 11/1977 | Grant | | 261/130 |
| 4,110,419 A | 8/1978 | Miller | | 261/142 |
| 4,146,597 A | 3/1979 | Eckstein et al. | | 261/104 |
| 4,155,961 A | 5/1979 | Benthin | | 261/104 |
| 4,201,204 A | 5/1980 | Rinne et al. | | 128/203.27 |
| 4,355,636 A | 10/1982 | Oetjen et al. | | 128/204.13 |
| 4,369,777 A | 1/1983 | Lwoff et al. | | 128/200.16 |
| 4,381,267 A | 4/1983 | Jackson | | 261/104 |
| 4,401,114 A | 8/1983 | Lwoff et al. | | 128/200.14 |
| 4,708,831 A | 11/1987 | Elsworth et al. | | 261/130 |
| 4,773,410 A | 9/1988 | Blackmer et al. | | 128/203.26 |
| 4,883,049 A | 11/1989 | McDonald | | 128/202.22 |
| 4,926,856 A | 5/1990 | Cambrio, Jr. et al. | | 128/203.26 |
| 5,172,686 A | 12/1992 | Anthony | | 128/203.16 |
| 5,195,515 A | 3/1993 | Levine | | 128/203.26 |
| 5,390,665 A | 2/1995 | Leach | | 128/203.25 |
| 5,640,951 A | 6/1997 | Huddart et al. | | 128/204.17 |
| 5,769,071 A | 6/1998 | Turnbull | | 128/203.12 |
| 5,897,526 A | 4/1999 | Vaillancourt | | 604/82 |
| 5,943,473 A | 8/1999 | Levine | | 392/401 |
| 5,970,210 A | 10/1999 | Anthony | | 392/386 |
| 6,102,037 A | 8/2000 | Koch | | 128/203.26 |
| 6,167,883 B1 | 1/2001 | Beran et al. | | 128/203.17 |
| 6,349,722 B1 | 2/2002 | Gradon et al. | | 128/203.17 |
| 6,367,472 B1 | 4/2002 | Koch | | 128/203.12 |
| 6,988,497 B2 | 1/2006 | Levine | | 128/203.27 |
| 7,322,566 B2 * | 1/2008 | Anthony | | 261/128 |
| 2005/0164025 A1 * | 7/2005 | Simonetti et al. | | 428/532 |
| 2007/0080104 A1 * | 4/2007 | Rautio | | 210/338 |
| 2007/0209425 A1 * | 9/2007 | Shibata et al. | | 73/40 |

FOREIGN PATENT DOCUMENTS

CA   2 098 132   10/2000
EP   1 507 567 B1   11/2006

OTHER PUBLICATIONS

Davide Chiumello et al., In Vitro and In Vivo Evaluation of a New Active Heat Moisture Exchanger; Jun. 28, 2004.

* cited by examiner

Primary Examiner — Charles Bushey
(74) Attorney, Agent, or Firm — Lorusso & Associates

(57) ABSTRACT

An apparatus for the transfer of mass and heat including a membrane having a hydrophilic surface and an opposing hydrophobic surface. The construction prevents transmission or leakage of fluids from one side of the membrane to the other regardless of pressure gradients within the membrane bubble point or water intrusion pressure range, but allows the transfer of vaporized fluid from one side of the membrane to the other.

19 Claims, 12 Drawing Sheets

MEMBRANE BASED CONTACTOR MODULE FOR MASS AND HEAT TRANSFER

FIELD OF THE INVENTION

The invention relates to membranes used to intermix, separate and/or introduce one fluid or gas into a second fluid or gas. More particularly, the invention concerns apparatus and methods for controlling the mixing of fluid vapor with gases such as air without allowing fluid droplets to pass into the air.

BACKGROUND OF THE INVENTION

To mix different liquids or a liquid with a gas in a controlled manner, porous membranes are often used as a barrier between the materials. A unidirectional pressure gradient from one side of the membrane to the other often determines the direction of flow of the materials through the membrane. The properties of the membrane itself also affect the flow of materials from one side of the membrane to the other.

Referring to FIG. 2, a prior art humidifier is shown generally as 30. The prior art humidifier includes a container 32 having a hydrophilic membrane 34 that divides container 30 into two chambers, 36 and 38. A fluid, such as water, is introduced into chamber 36 via an inlet 40 and exits the chamber via outlet 42. A second fluid or gas, such as air, is introduced into chamber 38 via a second inlet 46 and exits the chamber via a second outlet 44. The fluids may flow in either co-current or counter-current directions.

Membrane 34 has micro-pores that fill with water due to the hydrophilic nature of the material. To prevent water from entering the air chamber 38, chamber 38 must be maintained at a constant higher pressure than chamber 36. If the pressure gradient is not maintained, water droplets can migrate into the air chamber and be dispersed by the flow of air. This can be particularly onerous when the humidifier is used in a respiratory track therapy application in which water droplets can be carried undesirably into a patient's lungs.

Referring to FIG. 3, another prior art humidifier is shown generally as 50. This prior art humidifier includes a container 52 in which a hydrophobic membrane 54 is disposed. Membrane 54 divides container 52 into two chambers, 56 and 58. A fluid, such as water, is introduced into chamber 56 via an inlet 60 and exits the chamber via an outlet 62. A second fluid or gas, such as air, is introduced into chamber 58 via a second inlet 64 and exits via a second outlet 66. Due to the hydrophobic properties of membrane 54, the membrane's micro-pores are filled with air. To prevent air from leaking into water chamber 56, chamber 56 must be maintained at a constant higher pressure than chamber 58. Due to the limited characteristics of the membranes, pressure gradients must be constantly and precisely monitored and controlled to prevent unwanted migration of one fluid into the other.

Contemporary humidifiers used in respiratory track therapy applications are based on hydrophilic hollow fiber cartridges that employ sensitive pressure control to prevent water droplets from entering into the air stream and into the patient. A persistent problem with water droplet migration occurs when the units are idle. What is needed and desired is a humidifier that prevents water droplet migration independent of the apparatus' activity status and independent of pressure gradients. These and other objects of the invention will become apparent from a reading of the following summary and detailed description of the invention.

SUMMARY OF THE INVENTION

In one aspect of the invention, an apparatus for mass and heat transfer includes a container with a membrane deposited in the container so as to segment the container into two sections. The membrane has one hydrophilic surface bordering on and defining one section and a second opposing hydrophobic surface bordering on and defining a second section. Fluids introduced into the sections flow into the membrane but do not penetrate out the other side due to the opposite characteristics of the surfaces.

In another aspect of the invention, the membrane is a composite or laminate version comprised of two or more layers of membranes, each layer having a specific characteristic selected from hydrophilic, hydrophobic, oleo-philic and/or oleo-phobic. The membrane may be configured into sheet, pleated, multi-channel or honeycomb-shaped, plate-and-frame, and spiral versions, among others.

The apparatus may be used to humidify and heat air for respiratory tract therapies, gas absorption, selective transfer of specific components from a gas to a liquid or a liquid to a gas, liquid-liquid extractions, membrane distillation processes, immobilized liquid membrane systems and/or moving or flowing liquid membrane systems.

DETAILED DESCRIPTION OF THE INVENTION

Figure 1:
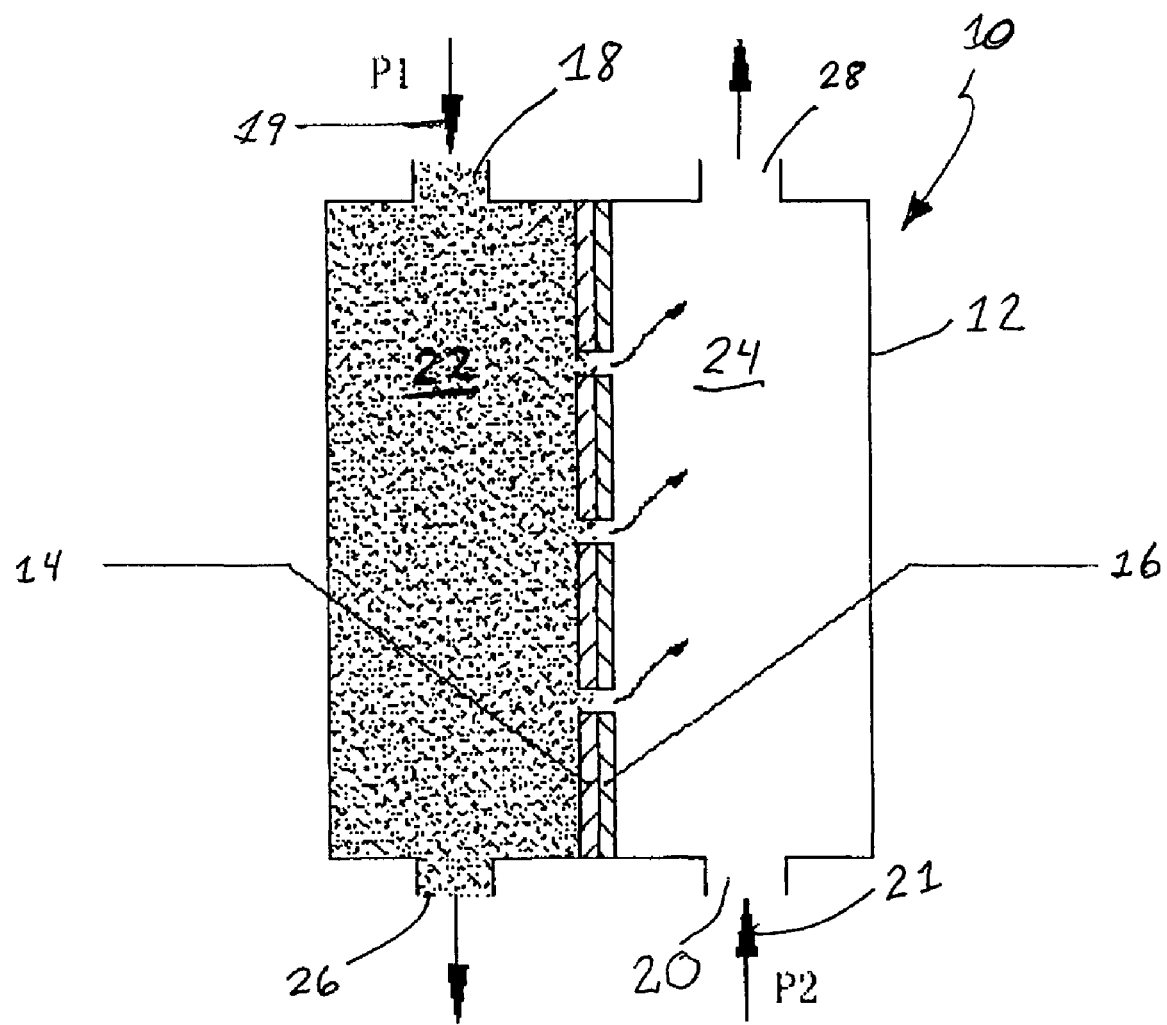
FIG. 1 is a sectional view of an apparatus and a composite membrane assembly according to one embodiment of the invention.

Referring to FIG. 1, in one aspect of the invention, a mass and heat transfer apparatus is shown generally as 10. Apparatus 10 includes a container 12 generally hollow and configured to hold a hydrophilic membrane 14 and an adjacent hydrophobic membrane 16. Each membrane has a face that interfaces with a face of the other membrane, the combination of which divides container 12 into two separate sealed compartments with the exception of dedicated inlets and outlets, described below, for the separate compartments. The membrane combination thus has a hydrophilic side and a hydrophobic side.

A first compartment 22 defined in part by membrane 14 has an inlet 18 in fluid communication with compartment 22, and an outlet 26 in fluid communication with compartment 22. A second compartment 24 defined in part by membrane 16 has an inlet 20 in fluid communication with compartment 24, and an outlet 26 in fluid communication with compartment 24.

A hydrophilic fluid 19, e.g., water, is introduced at a pressure P1 into compartment 22 via inlet 18. Pores contained in membrane 14 are wetted and filled by fluid 19 so as to reach the interface boundary between membrane 14 and membrane 16, which prevents the bulk flow of fluid to compartment 24.

Another fluid 21, e.g., air or oxygen, which may or may not be hydrophobic, but not hydrophilic, is infused at a pressure P2 (which may be less than, equal to or greater than P1), into compartment 24 via inlet 20. Pores contained in membrane 16 are wetted and filled by fluid 21 so as to reach the interface boundary between membrane 14 and membrane 16, which prevents the bulk flow of fluid 21 to compartment 22.

The hydrophobic nature of membrane 16 prevents the migration of hydrophilic fluid 19 into chamber 24. In addition, the hydrophilic nature of membrane 14 prevents the migration of fluid 21 into compartment 22 if fluid 21 is hydrophobic. Although bulk flow of fluid in either direction is prevented, the interface of membranes 14 and 16 allow the contact of fluid 19 and fluid 21 so as to allow for mass and heat transfer, e.g., the transfer of heat and vapor from fluid 19 into compartment 24.

Use of porous membranes creates a higher surface area for mass and heat transfer without the bulk flow or mixing of the two phases of fluids when introduced into apparatus 10. As used herein "fluid phase" shall mean any material infused into the apparatus in liquid or gaseous form including, but not limited to, atomized forms of liquid and/or solid materials.

Pore size contributes to the barrier effect. In general, the smaller the pore size, the higher the surface area, and the stronger the barrier effect or resistance to flow. If porosity is the same from one side of the membrane to the other— whether in a single membrane or multi-layer version—the smaller the pores, the better the contacting surface area at the hydrophilic/hydrophobic interface. For a given pore size, the prevention of bulk flow of a fluid from one compartment to another is maintained regardless of any pressure differential that does not exceed the bubble point pressure or maximum differential pressure of the hydrophilic membrane and/or the water intrusion pressure of the hydrophobic membrane.

An added benefit of a relatively small pore size, particularly with respect to the hydrophilic membrane, is the barrier effect on bacteria migration. Pore sizes from about 0.01 microns to about 50 microns provide this effect. More specifically, pore sizes less than about 0.22 micrometers provides a desirable bubble point and enhanced bacteria migration barrier effect.

This property holds true with respect to flow in either direction during operation of accessory devices connected to apparatus 10 such as medical humidifiers for respiratory track therapy, gas absorption into aqueous solutions and de-humidification of air into liquid desiccants. The same holds true if the accessory device is in standby mode when pressure differentials may not be monitored and controlled.

With respect to the foregoing property, it should be understood that the hydrophilic/hydrophobic nature of the membrane(s) is what prevents the bulk transfer of fluid; pore size sets the limiting points of prevention for the hydrophilic membrane's bubble point pressure and the hydrophobic membrane's intrusion pressure.

Figure 1A:
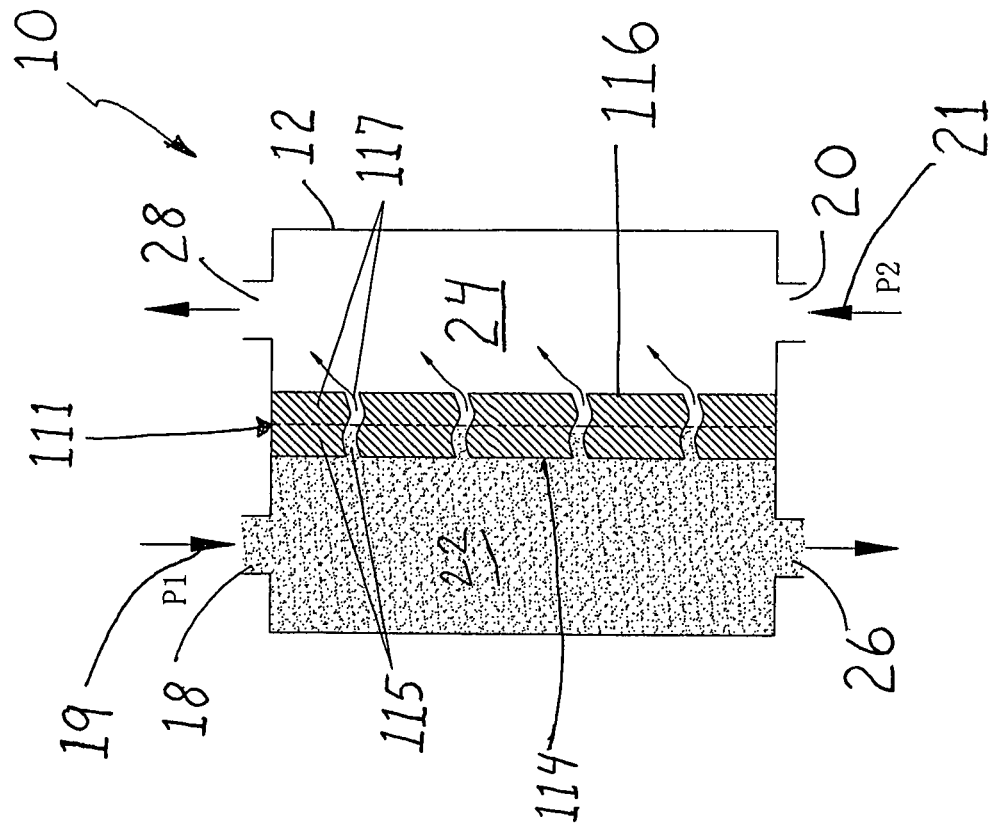
FIG. 1A is a sectional view of an apparatus and integral membrane assembly according to another embodiment of the invention.
Figure 2:
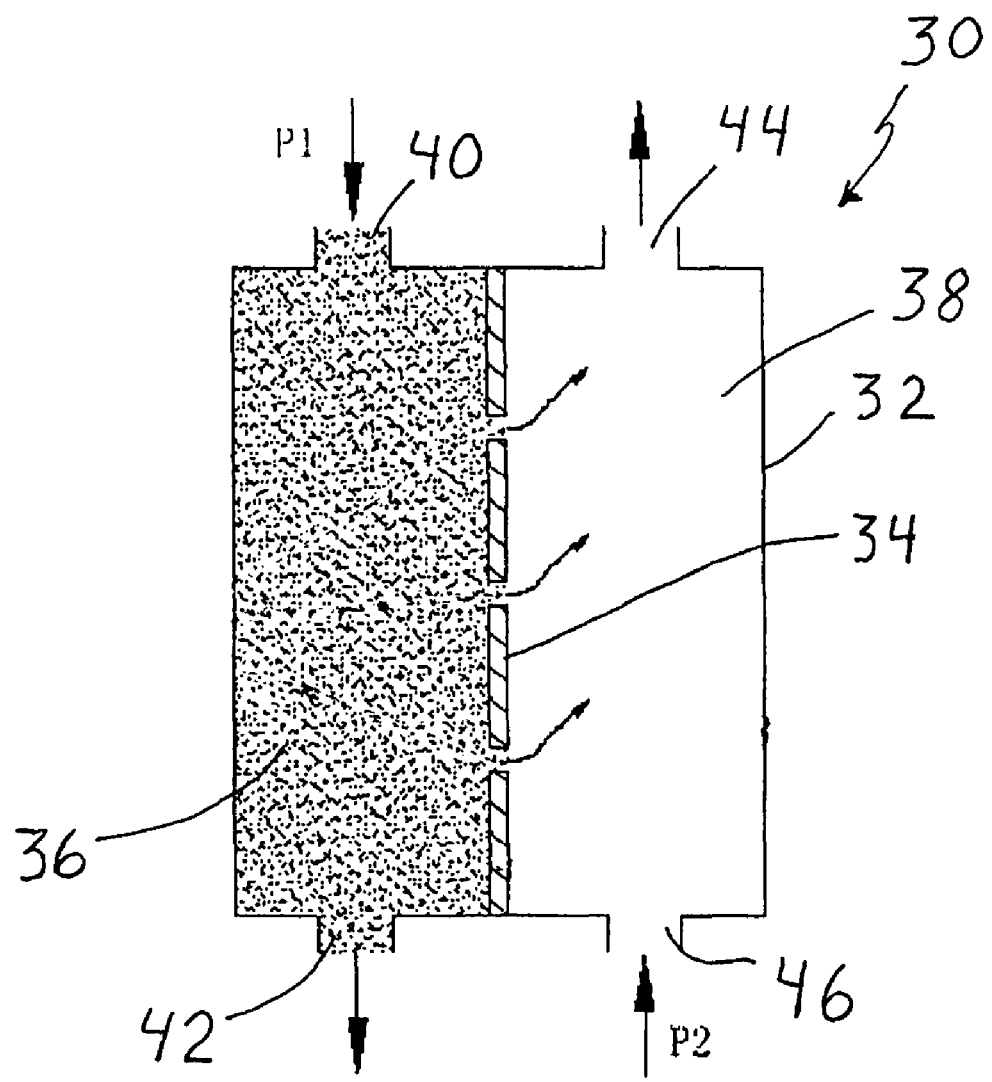
FIG. 2 is a sectional view of a prior art apparatus with a hydrophilic membrane.
Figure 3:
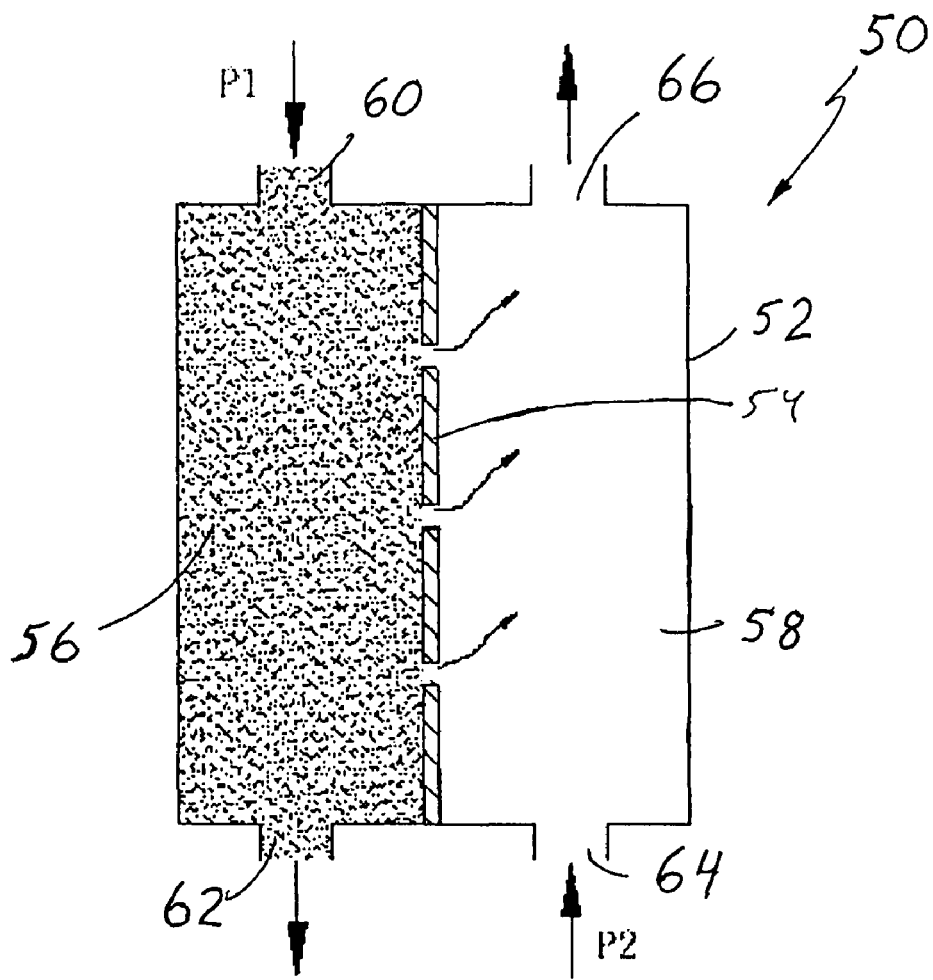
FIG. 3 is a sectional view of another prior art apparatus with a hydrophobic membrane.
Figure 4:
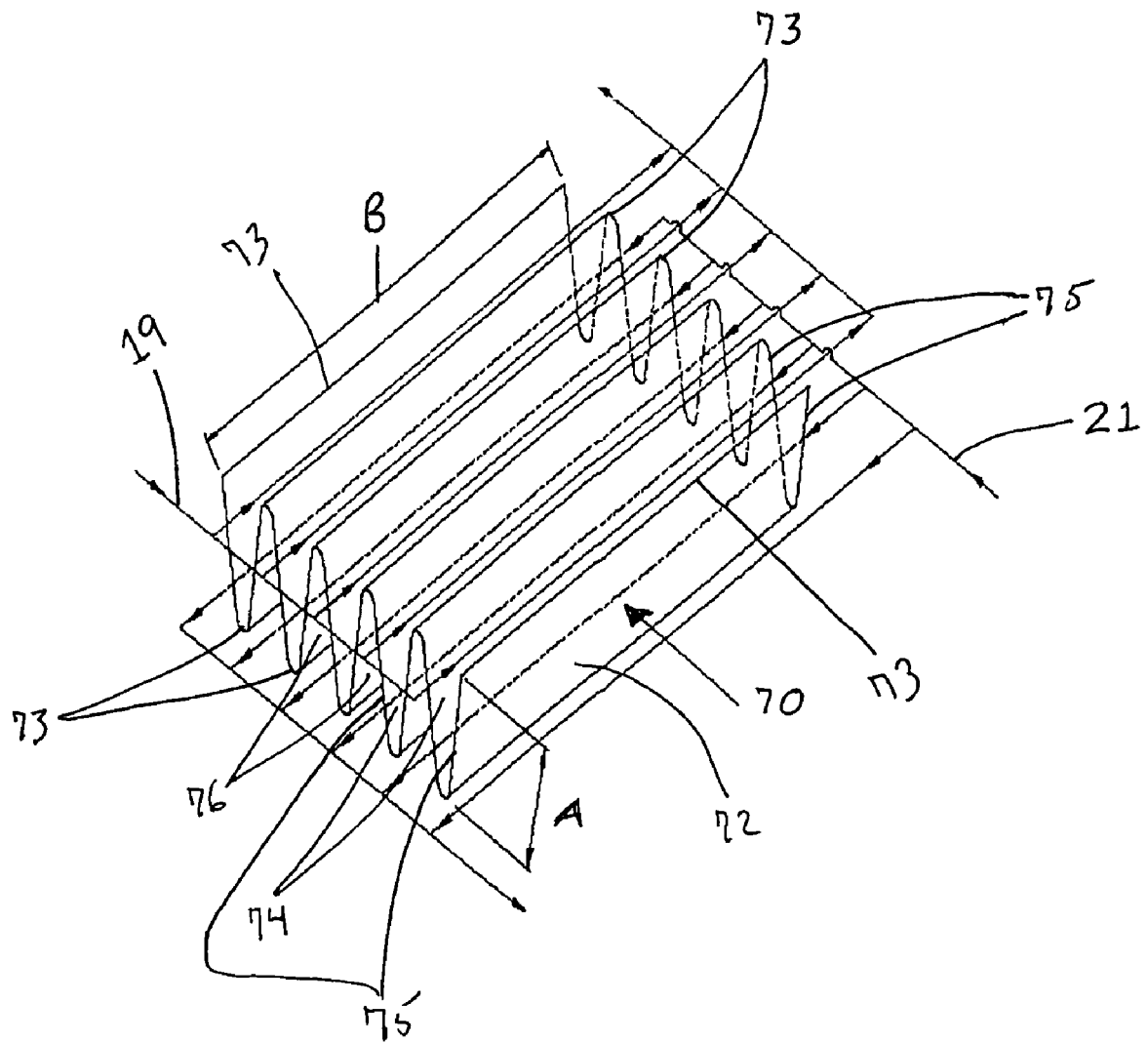
FIG. 4 shows a membrane in a pleated configuration according to one embodiment of the invention.

In another aspect of the invention as shown in FIG. 1A, a single membrane 111 provides the necessary hydrophilic/hydrophobic combination. In this embodiment, membrane 111 can be formed from a hydrophobic material 116 with one surface being modified to function as a hydrophilic surface 114 or formed from a hydrophilic material (not shown) with one surface being modified to function as a hydrophobic material. As shown in FIG. 1A, membrane 116 has pores 117 filled with fluid 21 that migrates up to the boundary between the unmodified portion of membrane 116 and hydrophilic surface 114. In contrast, surface 114 has pores 115 filled with fluid 19 that migrates to the same boundary as fluid 21.

In yet another aspect of the invention, the membrane component can be constructed as a composite or lamination of two membranes into a single integral membrane with opposite sides having different and/or opposed surface properties, i.e., one surface hydrophobic and the opposite hydrophilic. As used herein, composite membrane(s) shall mean a membrane formed by casting a top material onto a base material wherein the top material has a surface property, e.g., hydrophilic, hydrophobic, oleo-philic, and oleo-phobic, different than the surface property of the base material.

In one illustrative embodiment of a composite membrane, a polymer coat is cast onto a base membrane in the same manner well known in the art to create reverse-osmosis and nanofiltration membranes. The interface of the hydrophobic and hydrophilic layers is typically asymmetrical in cross section with no obvious boundaries between the layers unlike a laminated or stacked multi-layer membrane. Bulk fluid migration is limited to the depth of the surface on which the fluid interfaces. The functional surface area can be formed from polymeric and/or inorganic materials.

Figure 5:
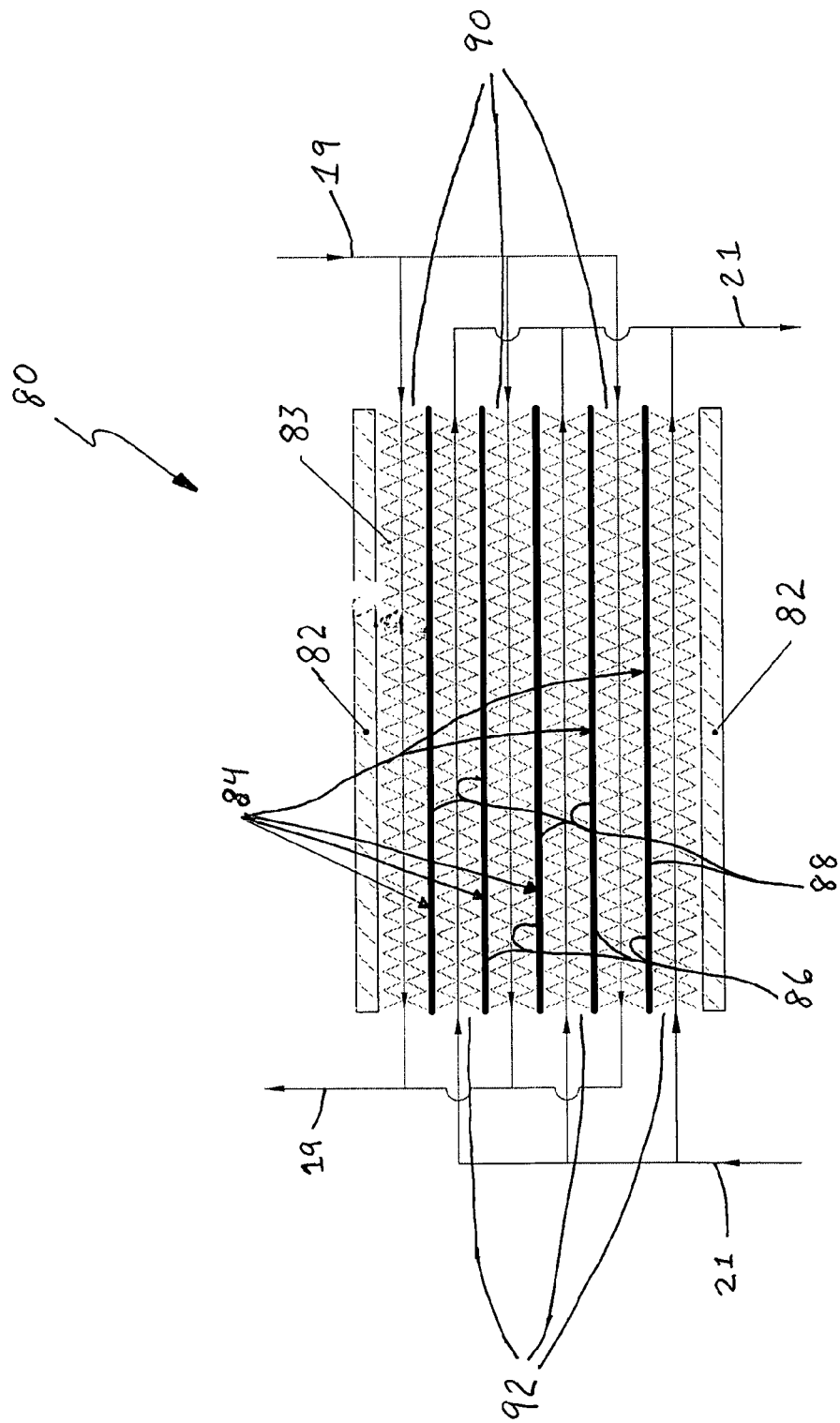
FIG. 5 shows a membrane in a stacked configuration according to another embodiment of the invention.
Figure 6:
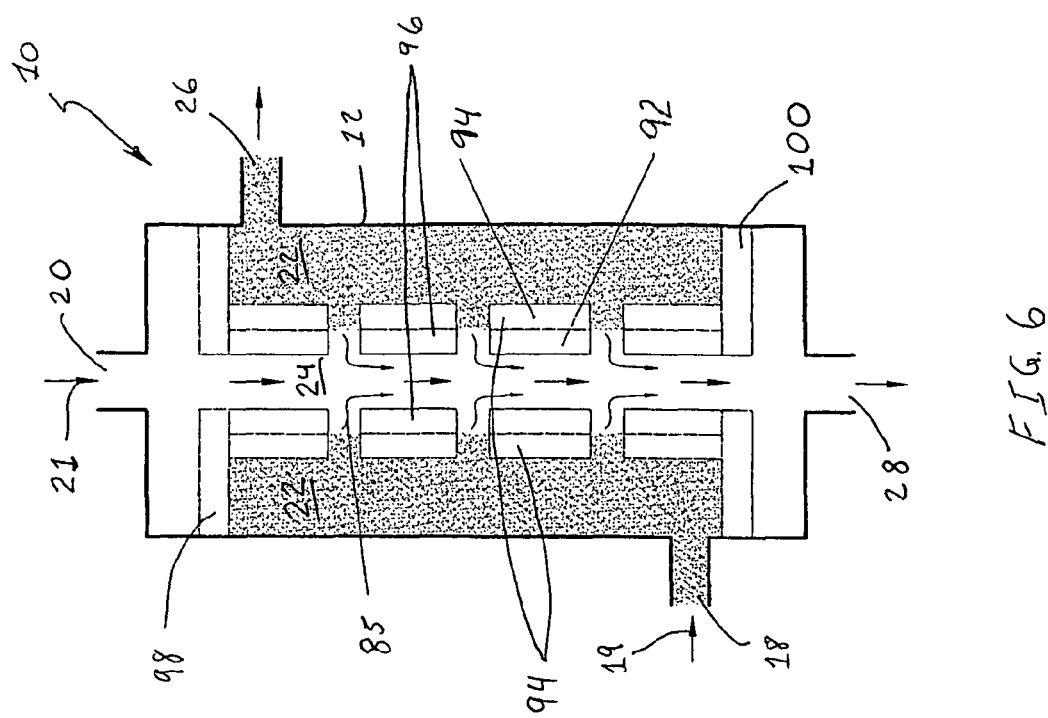
FIG. 6 is a sectional view of a container with a hollow fiber or tubular membrane according to yet another embodiment of the invention.
Figure 7:
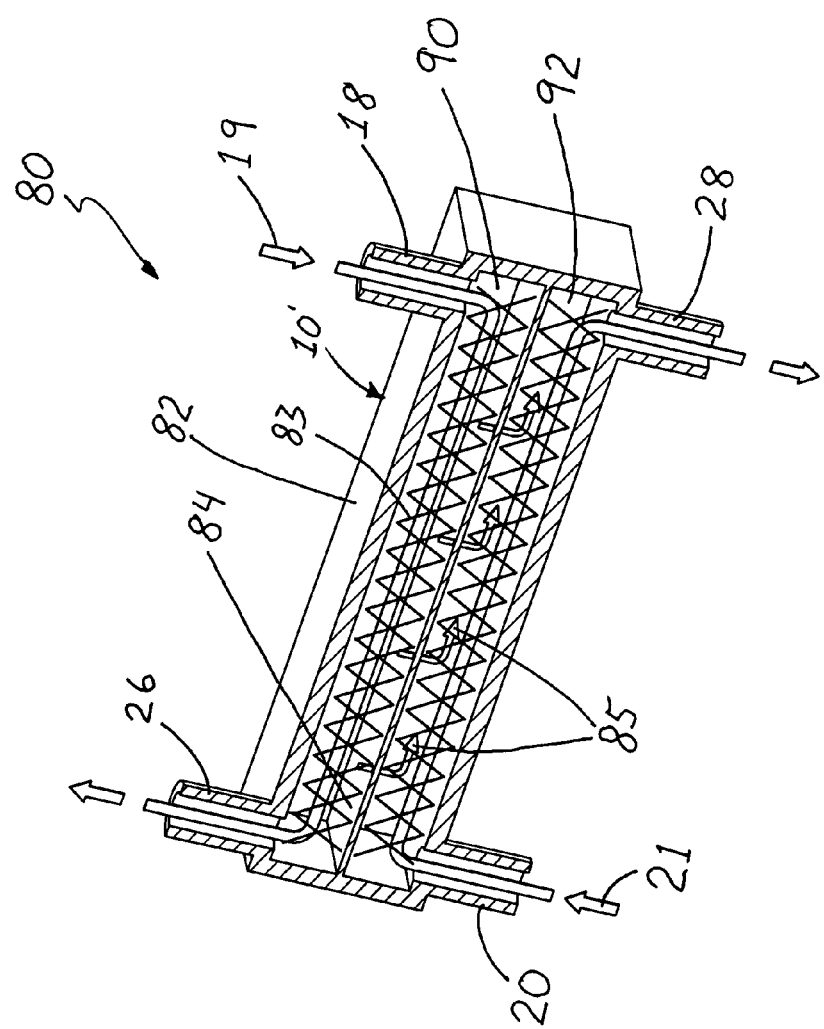
FIG. 7 is a sectional perspective view of a plate and frame assembly according to a further embodiment of the invention.

In a further alternate embodiment as shown in FIG. 6, the membrane can be constructed from hollow fibers or tubular forms with diameters ranging from about 30 microns to about 25 millimeters. Whether made from hollow fibers or porous sheet versions, the membrane in any of the recited constructions can be configured in flat sheets as shown in FIGS. 1 and 1A, pleated sheets as shown in FIGS. 4, 8-10, spiral-wound as shown in FIG. 11, multi-channel or honeycomb shaped, and/or plate-and-frame as shown in FIGS. 5 and 7. With any of the versions, the fluid flows can be either co-current or counter-current.

With respect to the multi-channel or honeycomb shaped version, the inner flow channels can range in size from about 0.2 millimeters to about 30 millimeters. With respect to the plate-and-frame configuration, the flow channels can have a width from about 100 microns to about 20 millimeters.

Material selection and channel size selection is determined by the acceptable or required bulk flow resistance through the channel. If too small a channel is selected, the flow pressure drop could be too high and require the liquid to be forced through the pores at the inlet side. Once a channel is selected, the material selection process is simplified as any of the materials described herein and variants thereof that can be used to form membranes with channels of the desired size can be selected.

If the apparatus is intended to be used in a respiratory humidification application, the pleated version of the membrane is particularly advantageous due to its relative ease of manufacture and availability in hydrophilic and hydrophobic varieties. It should be understood, however, that any of the different membrane embodiments may be used in a respiratory humidification application.

Referring again to FIG. 4, a pleated sheet configuration is shown. Membrane 70 is formed into a series of pleats 72 that form alternating channels. One set of channels 74 are dedicated to one fluid and a second set of channels 76 are dedicated to a second fluid. Membrane 70 can be secured in a container, such as container 12 (shown in FIG. 1), having any regular or irregular geometric cross-section shape including rectangular, circular, square, trapezoidal and the like.

Figure 8:
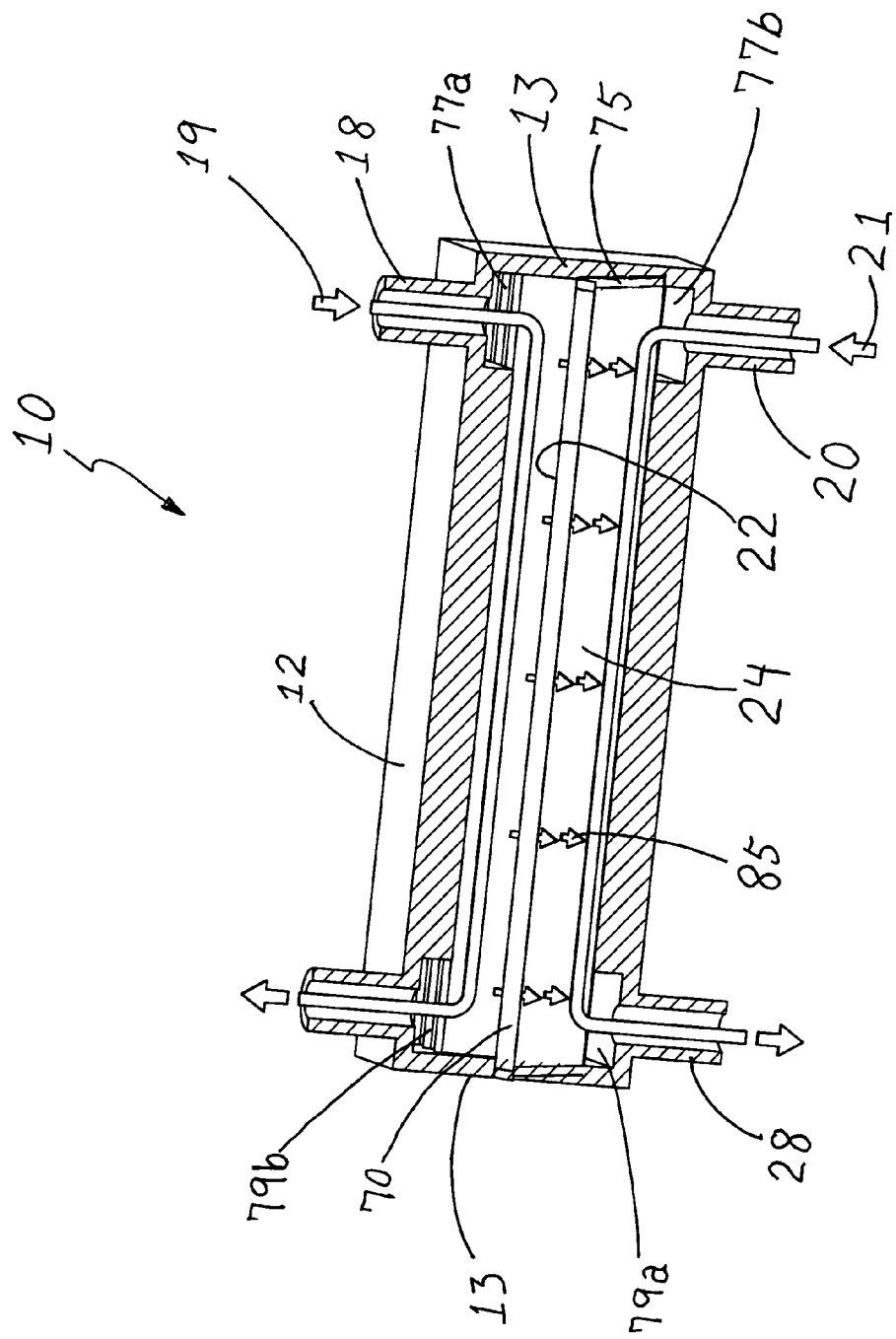
FIG. 8 is a side sectional perspective view of an apparatus with a pleated membrane according to one embodiment of the invention.
Figure 9:
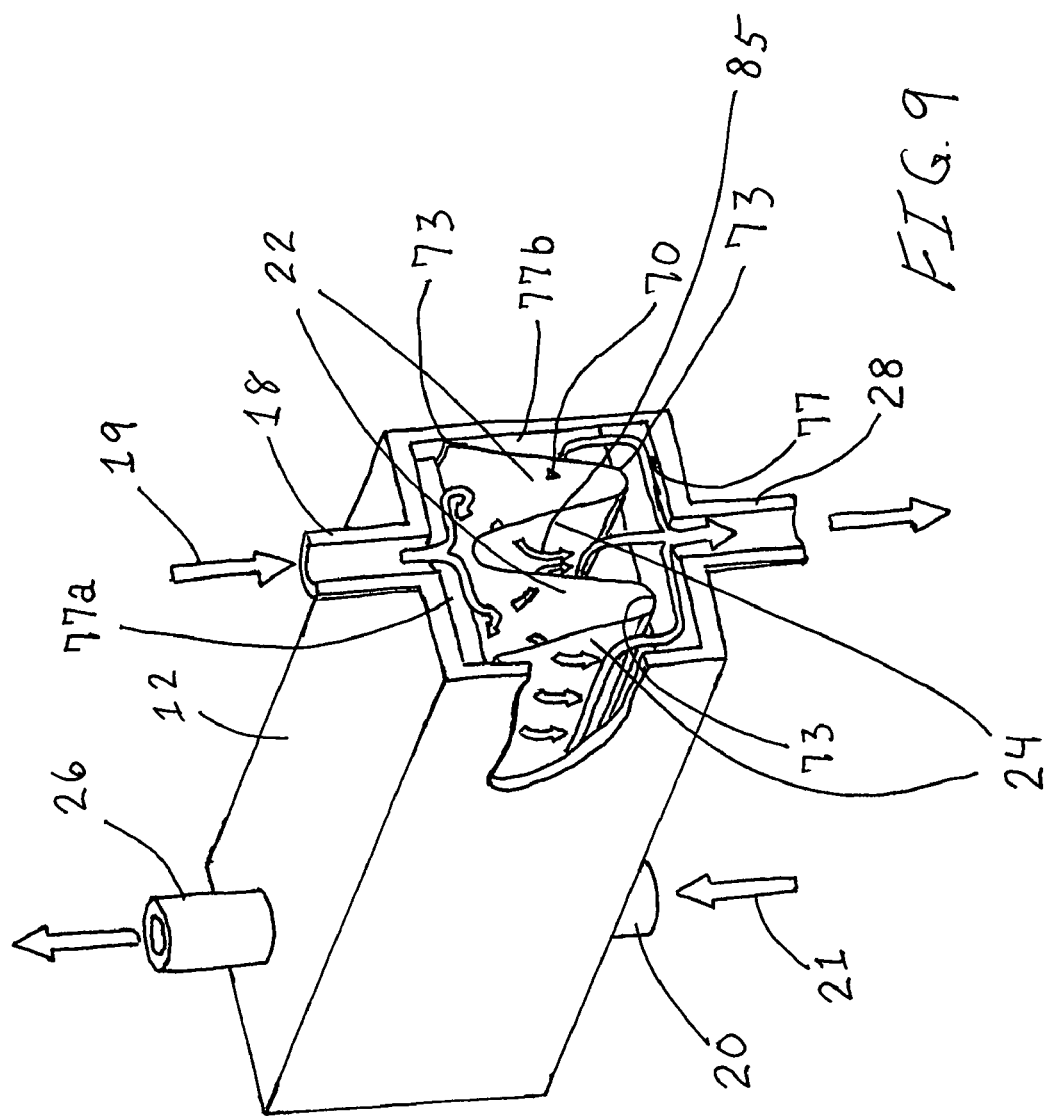
FIG. 9 is an end sectional perspective view of an apparatus with a pleated membrane according to one embodiment of the invention.

Referring to FIGS. 8 and 9, pleat edges 73 of membrane 70 are sealed to the side walls of container 12 with membrane ends 75 sealed to container end plates 13 (shown in FIG. 8). Pleat edges 73 can be sealed to the container side walls by ultrasonic (vibration), thermal, and/or adhesive methods. Suitable adhesives include epoxy, polyurethane, and hot-melt adhesives. Membrane ends 75 may be sealed to end plates 13 with adhesives such as epoxy, polyurethane, hot-melt adhesives, or sealed by thermal melt potting. In this manner, two separate convoluted chambers are created in container 12.

Fluid 19 access to the convoluted sections of chamber 22 is provided by distribution recess 77 in fluid communication with inlet 18 and chamber 22. Distribution recess 77 is defined by the recessed walls of container 10 and the membrane ends 75. A first portion 77a of distribution recess 77 connects inlet 18 in fluid communication with chamber 22. A second portion 77b of distribution recess 77 connects outlet 28 with chamber 24 to allow for the out flow of fluid 21. Distribution recess 77 is formed at an end of container 12 adjacent to inlet 18.

Fluid 21 access to convoluted sections of chamber 24 is provided by distribution recess 79 in fluid communication with inlet 20 and chamber 24. Distribution recess 79 is defined by the recessed walls of container 10 and membrane ends 75. A first portion 79a of distribution recess 79 connects inlet 20 in fluid communication with chamber 24. A second portion 79b of distribution recess 79 connects outlet 26 with chamber 22 to allow for the out flow of fluid 19. Distribution recess 79 is formed at an end of container 12 adjacent to inlet 20.

Figure 10:
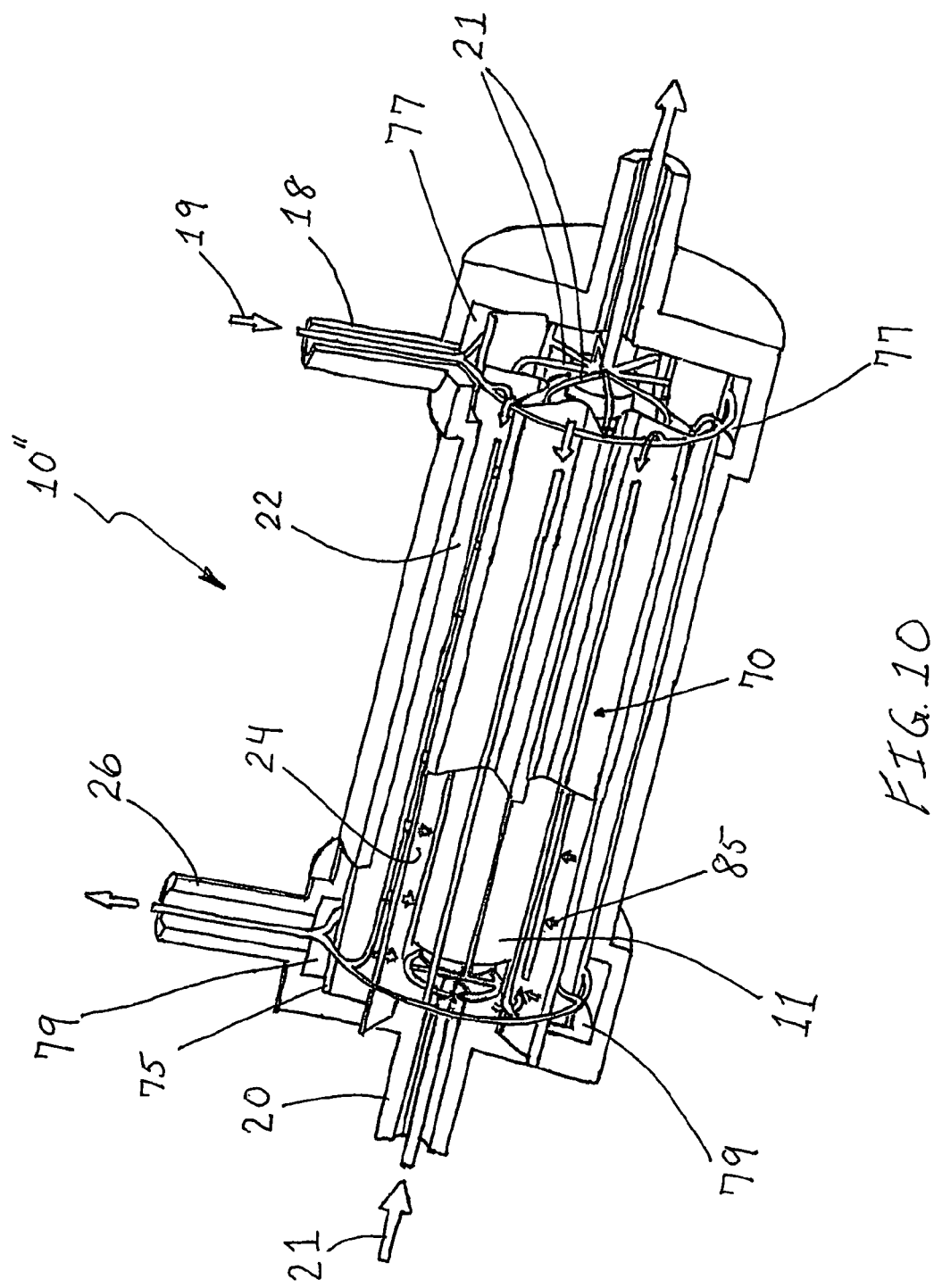
FIG. 10 is a side sectional perspective view of a cylindrical apparatus with a pleated membrane according to a yet further embodiment of the invention.
Figure 11:
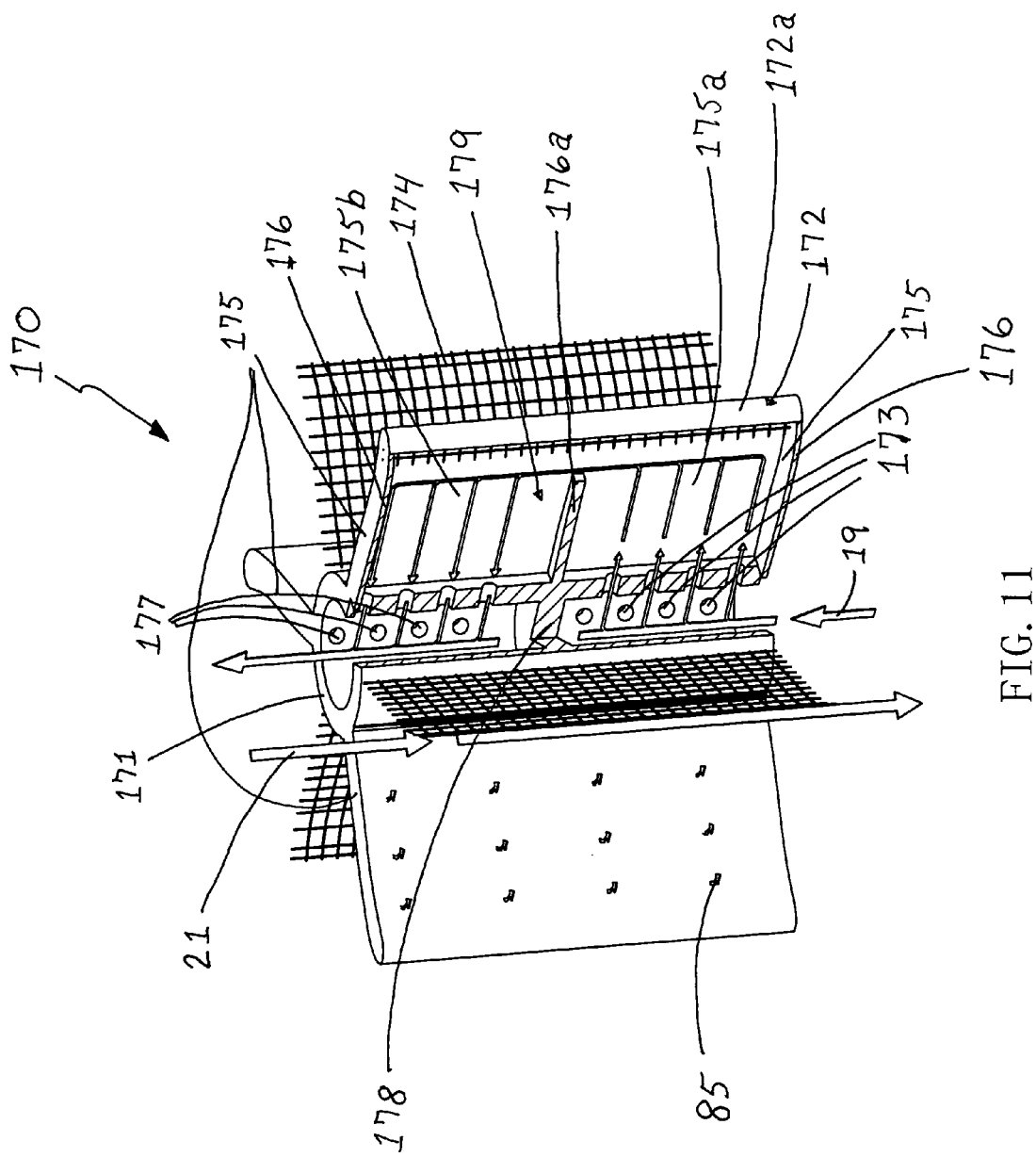
FIG. 11 is a partial sectional perspective view of a spiral wound membrane according to a still further embodiment of the invention.

In another pleated embodiment shown in FIG. 10, pleated membrane 70 is placed in cylindrical container 10". For clarity and ease of reference, similar elements in different embodiments have the same reference character numbers in either primed or unprimed form. Container 10" includes an inner hollow cylinder 11 concentric to the wall of container 10". Membrane 70 is sandwiched between cylinder 11 and cylinder 10". As with the other pleated embodiments, ends 75 are sealed to the ends of cylinder 10". Fluid 19 enters inlet 18, flows into distribution recess 77, flows through chamber 22 and exits outlet 26.

Fluid 21 enters via inlet 20, which is in communication with the inside of cylinder 11. Cylinder 11 is in fluid communication with a portion of distribution recess 77, which, in turn, is in fluid communication with chamber 24. Fluid 21 flows through distribution recess 77 into chamber 24 where it receives vapor 85 that migrates through membrane 70 and exits out of outlet 28, as shown in FIG. 10.

With either pleated version, pleat height, designated as A, can be from about 2 mm to about 100 mm and the pleat width, designated as B, can range from about 5 mm to about 1000 mm. These ranges are given for illustrative purposes only with respect to respiratory therapy applications and may be modified to meet the requirements of a particular application. In like fashion, the number of pleats can vary considerably depending on the application.

Membrane 70 can be formed from a single layer with one surface treated to have the opposite physical property from the opposite untreated surface or can be formed as a composite of two or more membranes with each membrane having a different physical property, i.e., hydrophilic, hydrophobic, oleo-phylic and/or oleo-phobic.

Referring now to FIGS. 5 and 7, a plate-and-frame configuration 80 is shown in which multiple membranes 84 are implemented to provide structural and functional barriers between two fluids. As shown in FIG. 7, side walls 82 of container 10' encapsulate the membrane layers 84 and provide a sealed environment. Layers 84 are separated by spacers 83 with membrane ends sealed with adhesive, thermal plastic, ultrasonic and/or vibration methods. Spacer 83 thickness may be from about 0.1 mm to about 10 mm.

Spacer 83 may be woven or extruded netting formed from any polymeric material. Alternatively, they may be spun-bound or melt-blown non-woven fabrics, such as Typar® or Reemay® (both BBA Nonwovens). Extruded netting versions by DelStar Technologies, Inc. may also be used. All the referenced versions are commonly used in filter and membrane device applications as is well know in the art.

Each membrane 84 has a hydrophilic side 86 and a hydrophobic side 88. Membranes 84 are oriented to adjacent membranes so that surfaces with like surface properties are adjacent to each other. This configuration creates hydrophilic channels 90 and hydrophobic channels 92. Fluid access to the respective channels is provided by dedicated inlets and distribution sections such as those used with respect to the embodiment shown in FIG. 4.

Membranes 84 can be single layer with one surface treated to have a surface property different from the surface property of the untreated surface or can be multiple layers with each layer having surfaces with different surface properties from the other layers.

In a yet further embodiment, multiple layers may be used to create membrane 84 with the same surface physical properties with one exterior surface of membrane 84 treated to have a surface property different than the opposite exterior surface of membrane 84. The plate-and-frame configuration functions the same as the other configurations in that a hydrophilic fluid such as water is introduced into the hydrophilic channels 90 and a second fluid or gas, such as air, is introduced into the hydrophobic channels 92. Subject to the limitations described herein with respect to bubble point pressure and water intrusion pressure, as with the other configurations, pressure gradients do not affect the barrier effect of the hydrophilic/hydrophobic membranes 84, but allow for mass and heat transfer from one fluid column to the other including the passage of vapor 85.

Referring now to FIG. 6, container 10 includes a series of hydrophilic hollow tubes 94 stacked in a concentric arrangement against a series of hydrophobic hollow tubes 96, the combination positioned away from the walls of container 10 so as to form two sealed cylindrical compartments 22 and 24. The ends of the membranes are sealed via a top sealing ring or tube sheet 98 and a bottom sealing ring or tube sheet 100. Each sealing ring has a central bore to allow fluid communication between inlet 28, compartment 24 and outlet 20.

As with the other embodiments, fluid 19, e.g., water, enters chamber 22 and infuses into membrane 94 until saturation. Vapor 85 formed from fluid 19 migrates into compartment 22 and mixes with second fluid 21, e.g., air, and is transported with the air through a larger assembly such as a respiratory tract humidifier (not shown). As with the other embodiments, pressure gradients do not impact the barrier effect of the hydrophilic/hydrophobic hollow tube combination.

Referring now to FIG. 11, a spiral wound membrane apparatus 170 is shown. A plurality of membrane sections 172 are fixed to or integral with a central tube 171. Sections 172 are disposed in a radial arrangement around tube 171. Each section 172 includes a membrane 172a disposed on a membrane frame 179. Frame 179 includes seal lines 176 to which membrane 172a is secured. Edge seals 175 define the top and bottom edges of sections 172 and combine with membrane 172a and seal lines 176 to form two separate chambers 175a and 175b in each section 172. A plurality of inlet apertures 173 in fluid communication with the inside of tube 171 connects tube 171 to intake chamber 175a. Chambers 175a and 175b are not sealed from each other as a central seal line 176a does not extend the full width of section 172. A plurality of outlet apertures 177 connect chamber 175b with the inside of tube 171.

Fluid 19 flows into tube 171 and flows through inlet apertures 173 into chamber 175a. Fluid 19 then flows around central seal line 176a into chamber 175b. While flowing through the chambers, vapor 85 migrates though membrane 172a into spaces formed between adjacent membrane sections 172. Fluid 19 then flows into outlet apertures 177 into tube 171 and out of tube 171.

A membrane spacer 121 is provided between adjacent membrane sections 172. Spacer 121 maintains adjacent membrane layers apart to allow fluids to flow between the membranes without excessive resistance. This is particularly important for the configurations described herein including the spiral-wound configuration, which have tightly stacked or tightly wound layers. Fluid 21 is infused between sections 172 and mixes with vapor 85 before exiting apparatus 170.

The membranes or the functional surfaces of the membranes in a composite or single membrane embodiment have thicknesses from about 0.01 microns to about 5000 microns. Membrane pore sizes range from about 0.001 microns to about 1000 microns. The surface properties of opposing surfaces of combined membranes, composite membranes or single-layer membranes can each exhibit one of the following characteristics: hydrophilic, hydrophobic, oleo-phylic, or oleo-phobic. It should be understood that opposing surfaces of a membrane system, regardless whether a single layer or a dual layer, must not have the same characteristic; each must have a characteristic different from the characteristic of the opposing surface.

The membranes may be made from a variety of polymeric, metallic, ceramic materials or composites of the three. For flat sheet membranes used in the pleated, and plate-and-frame configurations, the membranes can be placed in the container without any thermal treatment, or can be spot-welded or spot laminated to improve ease of handling in the assembly process. Such treatment is not required to enhance or achieve the desired performance.

Hydrophobic membranes can be made from one or more nano-porous or micro-porous, naturally hydrophobic fluoro-polymer based membranes such as expanded Polytetrafluoroethylene (Teflon® PTFE) with or without lamination, phase inversion formed polyvinylidene fluoride (PVDF), perfluoroalkoxy (PFA) and its derivatives, Ethylene-clorotrifluoro-ethylene copolymer (ECTFE), micro-porous carbon and mixtures thereof. Other material options for the hydrophobic membranes include nano-porous and micro-porous, naturally hydrophobic polyolefin based membranes selected from polypropylene (PP), high density polyethylene (HDPE), ultra high molecular weight polyethylene (UHMWPE or UPE) and mixtures thereof. Any commercial forms of porous polyethylene membranes of any molecular weight can be used.

Still further material options include one or more surface modified polyethersulfone (PES), polysulfone (PS), Nylon 6, Nylon 66, regenerated cellulose, mixed esters of cellulose, polycarbonate, polyester membranes and mixtures thereof.

Hydrophilic membranes can be made from one or more surface-property-modified nano-porous or micro-porous fluoro-polymer based membranes including expanded Polytetrafluoro-ethylene (Teflon® PTFE) with or without lamination, phase inversion formed polyvinylidene fluoride (PVDF), perfluoroalkoxy (PFA) and its derivatives, Ethylene-clorotrifluoroethylene copolymer (ECTFE) and mixtures thereof. Other materials include modified, nano-porous and micro-porous polyolefin based membranes made from polypropylene (PP), high density polyethylene (HDPE), ultra high molecular weight polyethylene (UHMWPE or UPE) and mixtures thereof.

Still further materials include one or more naturally hydrophilic polyethersulfone (PES), polysulfone (PS), Nylon 6, Nylon 66, regenerated cellulose, mixed esters of cellulose, polycarbonate, ceramic, polyester membranes and mixtures thereof.

When used in a respiratory tract therapy assembly, the apparatus allows for the controlled vaporization of water into air, or humidification of air.

In this manner, water vapor is introduced into the air column without the bulk transfer of water into the air or air bubbling into the water side regardless of pressure gradients in either direction, provided that the pressure gradient is within the hydrophilic membrane's water bubble point and the hydrophobic membrane's water intrusion pressure.

If the pressure gradient exceeds the hydrophilic membrane's water bubble point, air will force the water out of the hydrophilic membrane's pores and will enter the water chamber. If the water pressure gradient exceeds the water intrusion pressure of the hydrophobic membrane, water will enter the pores of the hydrophobic membrane and infuse into the air chamber. The smaller the membrane pore size, the higher the water bubble point and the water intrusion pressure.

If a 0.22 micron or smaller pore size is used for the hydrophilic membrane, the water bubble point should be greater than about 2 bars, which will have the added benefit of preventing the presence of any bacteria in the water side from migrating from the water side to the air side. For the hydrophobic membrane, a pore size should be selected to exceed a water intrusion pressure in the range of from about 0.3 to about 4 bars.

The selection of pore size is dependent on the material selected for the membrane as the surface property differences of different materials will affect pore size threshold. Ultimately, the goal is to select a pore size for a given material that will meet the required minimum bubble point and/or intrusion pressure for a particular application. In one embodiment, the pore sizes for the hydrophilic membrane can range from about 0.01 to about 1.2 microns. For the hydrophobic membrane, the pore sizes can range from about 0.01 to about 10 microns. A lower pressure threshold for the hydrophobic membrane is acceptable particularly when used in a respiratory tract application as the water pressure used in such an application is relatively low and usually below 4 bars.

Referring again to FIG. 1, in one embodiment, water 19 is introduced into compartment 22 on the hydrophilic side. Water 19 enters and saturates the pores of membrane 14. Water migration is arrested when water 19 reaches the interface between membrane 14 and membrane 16. Concurrently or consecutively with water 19, air 21 is introduced into compartment 24 and enters and saturates the pores of membrane 16.

Migration of air 21 into membrane 14 is prevented by water 19, due to the saturation of membrane 14. This effect holds when a pressure gradient is introduced with a higher pressure on the air side so long as the bubble point of the hydrophilic membrane is not surpassed or equaled. Water vapor formed at the hydrophilic membrane/hydrophobic membrane interface can migrate into the air column against a pressure gradient. The vapor passes through the pores in hydrophobic membrane 16 into the air/gas stream, which provides humidified air or a formulated gas stream if a medicament is the fluid introduced into the hydrophilic chamber. This system also provides a means to achieve a desired temperature by controlling the water temperature and the residence time of the air/gas in the apparatus.

If a higher pressure is introduced on the water side, the hydrophobic nature of membrane 16 will prevent the bulk flow of water 19 into membrane 16 and compartment 24 as long as the pressure is below the intrusion pressure of the hydrophobic membrane. Accordingly, the apparatus provides substantial flexibility in the control of fluid-fluid and/or fluid-gas migration regardless of pressure gradients.

The apparatus is particularly advantageous in respiratory tract therapies, general humidification, and as an absorber or membrane reactor when certain molecule(s) from the gas stream are absorbed by, and/or react with the water or other formulated aqueous solution that interfaces with the gas at the hydrophilic/hydrophobic interface. Further uses include liquid degassing and stripping application, e.g., removal of volatile organic compounds from aqueous solutions or removal of oxygen or other dissolved gas molecules from the aqueous/hydrophilic solution. A still further use is liquid-liquid extraction processes, e.g., extraction of heavy metals from aqueous solutions by solvent with metal chelating agents.

An additional application is to use the apparatus in bioreactors and carrier-facilitated transport processes, or artificial lungs for blood oxygenation and carbon dioxide removal. If the hydrophilic membrane is also designed to be oleo-phobic, the apparatus may be used in aqueous and oil solution extraction processes.

With respect to composite membrane systems, i.e., membrane systems made from two or more membranes, the membranes made be stacked together and held together via physical (spot weld by ultrasonic), thermal (heating to allow materials to melt and bind while cooling), or chemical methods (chemical adhesives). In the case of single membranes, one side of the membrane can be chemically or physically modified to have a surface property different from the opposing unaltered surface.

Surface modification of a hydrophobic membrane can be accomplished by cross-linking amine monomers, or cross-linking PVA on hydrophobic membranes to make them hydrophilic. Examples of membrane surface modifications are described in U.S. Pat. Nos. 6,159,369, 5,376,274 and 5,554,414, all of which are incorporated herein by reference.

While the present invention has been described in connection with several embodiments thereof, it will be apparent to those skilled in the art that many changes and modifications may be made without departing from the true spirit and scope of the present invention. Accordingly, it is intended by the appended claims to cover all such changes and modifications as come within the true spirit and scope of the invention.

What I claim as new and desire to secure by United States Letters Patent is:

1. An apparatus for mass and heat transfer comprising:
    a container defining a general chamber;
    a porous membrane secured in the general chamber, wherein the membrane has a first surface having a first thickness wherein the first surface is at least partially hydrophilic and a second surface having a second thickness wherein the second surface is at least partially hydrophobic, wherein the membrane is positioned in the container to separate the general chamber into a first chamber configured to receive a hydrophilic fluid or gas and a second chamber configured to receive a hydrophobic fluid or gas, wherein the first chamber is defined by portions of the container in combination with the first surface and wherein the second chamber is defined by different portions of the container in combination with the second surface;
    a first entry port connected to, and in fluid communication with, the first chamber;
    a first exit port connected to, and in fluid communication with, the first chamber;
    a second entry port connected to, and in fluid communication with, the second chamber;
    a second entry port connected to, and in fluid communication with, the second chamber; and,
    the membrane having pore sizes from about 0.01 microns to about 50 microns.

2. The apparatus of claim 1 wherein the first surface is connected to the second surface by a connection method selected from the group consisting of stacking, physical and thermal lamination, chemical bonding and combinations thereof.

3. An apparatus for mass and heat transfer comprising:
    a container having a general chamber;
    a hydrophilic membrane positioned in the container;
    a hydrophobic membrane positioned in the container adjacent to the hydrophilic membrane, wherein the hydrophilic and hydrophobic membranes combine to separate the general chamber into a first chamber and a second chamber, wherein the first chamber is defined by portions of the container in combination with the hydrophilic membrane and the second chamber is defined by different portions of the container in combination with the hydrophobic membrane, wherein the first chamber is configured to receive a hydrophilic fluid or gas and the second chamber is configured to receive a hydrophobic fluid or gas;
    a first entry port connected to, and in fluid communication with, the first chamber;
    a first exit port connected to, and in fluid communication with, the first chamber;
    a second entry port connected to, and in fluid communication with, the second chamber;
    a second entry port connected to, and in fluid communication with, the second chamber; and,
    the membrane having pore sizes from about 0.01 microns to about 50 microns.

4. The apparatus of claim 3 wherein the hydrophilic membrane is connected to the hydrophobic membrane by a connection method selected from the group consisting of stacking, physical and thermal lamination, chemical bonding or combinations thereof.

5. The apparatus of claim 1 wherein the membrane is hydrophilic and the second surface is modified to be hydrophobic.

6. The apparatus of claim 1 wherein the membrane is hydrophobic and the first surface is modified to be hydrophilic.

7. The apparatus of claim 1 wherein the membrane is configured in a form selected from the group consisting of flat sheet, pleated sheet, spiral wound configuration, hollow fiber, tubular, multi-channel, honeycomb and combinations thereof.

8. The apparatus of claim 3 wherein the membranes are configured in a form selected from the group consisting of flat sheet, pleated sheet, spiral wound configuration, hollow fiber, tubular, multi-channel, honeycomb and combinations thereof.

9. The apparatus of claim 1 wherein the membrane has a thickness from about 0.1 microns to about 5000 microns and has a pore size from about 0.001 microns to about 1000 microns.

10. The apparatus of claim 1 wherein the first thickness and the second thickness are from about 0.01 microns to about 5000 microns.

11. The apparatus of claim 3 wherein the hydrophobic membrane is a nano-porous and micro-porous, naturally hydrophobic fluoro-polymer selected from the group consisting of expanded Polytetrafluoro-ethylene (Teflon® PTFE) with or without lamination, phase inversion formed polyvinylidene fluoride (PVDF), perfluoroalkoxy (PFA) and its derivatives, Ethylene-clorotrifluoroethylene copolymer (ECTFE), micro-porous carbon and mixtures thereof.

12. The apparatus of claim 3 wherein the hydrophilic membrane is derived from a modified, nano-porous and micro-porous fluoro-polymer selected from the group consisting of expanded Polytetrafluoro-ethylene (Teflon® PTFE) with or without lamination, phase inversion formed polyvinylidene fluoride (PVDF), perfluoroalkoxy (PFA) and its derivatives, Ethylene-clorotrifluoroethylene copolymer (ECTFE) and mixtures thereof.

13. The apparatus of claim 3 wherein the hydrophobic membrane is a nano-porous and micro-porous, naturally hydrophobic polyolefin based membranes selected from the group consisting of polypropylene (PP), high density polyethylene (HDPE), ultra high molecular weight polyethylene (UHMWPE or UPE) and mixtures thereof.

14. The apparatus of claim 3 wherein the hydrophilic membrane is derived from a modified, nano-porous and micro-porous polyolefin based membrane selected from the group consisting of polypropylene (PP), high density polyethylene (HDPE), ultra high molecular weight polyethylene (UHMWPE or UPE) and mixtures thereof.

15. The apparatus of claim 3 wherein the hydrophilic membrane is derived from one or more naturally hydrophilic polyethersulfone (PES), polysulfone (PS), Nylon 6, Nylon 66, regenerated cellulose, mixed esters of cellulose, polycarbonate, ceramic, polyester membranes and mixtures thereof.

16. The apparatus of claim 3 wherein the hydrophobic membrane is derived from one or more surface modified polyethersulfone (PES), polysulfone (PS), Nylon 6, Nylon 66, regenerated cellulose, mixed esters of cellulose, polycarbonate, polyester membranes and mixtures thereof.

17. An apparatus for air humidification or gas phase therapy formulation comprising:
a container;
a hydrophilic membrane positioned in the container;
a hydrophobic membrane adjacent to the hydrophilic membrane, wherein the membranes are formed in a pleated configuration and, and wherein portions of the container and the hydrophilic membrane define a first chamber and different portions of the container and the hydrophobic membrane define a second chamber sealed from the first chamber;
a first entry port connected to, and in fluid communication with, the first chamber;
a first exit port connected to, and in fluid communication with, the first chamber;
a second entry port connected to, and in fluid communication with, the second chamber; and,
a second entry port connected to, and in fluid communication with, the second chamber.

18. The apparatus of claim 3 further comprising:
a first inlet attached to, and in fluid communication with the first chamber;
a first outlet attached to and in fluid communication with the first chamber;
a second inlet attached to and in fluid communication with the second chamber;
a second outlet attached to and in fluid communication with the second chamber, wherein the first chamber is configured to receive a first fluid and the second chamber is configured to receive a second fluid wherein the membranes act as a barrier between the two chambers.

19. The apparatus of claim 17 wherein the hydrophilic membrane has pore sizes from about 0.01 microns to about 50 microns.

* * * * *